(12) United States Patent
Zanthoff et al.

(10) Patent No.: US 8,680,356 B2
(45) Date of Patent: Mar. 25, 2014

(54) CATALYST AND PROCESS FOR PREPARING ISOOLEFINS

(75) Inventors: Horst-Werner Zanthoff, Muelheim a.d. Ruhr (DE); Dietrich Maschmeyer, Recklinghausen (DE); Thomas Quandt, Marl (DE); Franz Nierlich, Marl (DE); Silvia Santiago Fernandez, Oviedo (ES); Stephan Houbrechts, Duffel (BE); Georg Skillas, Hanau (DE); Kurt-Alfred Gaudschun, Recklinghausen (DE)

(73) Assignee: Evonik Oxeno GmbH, Marl (DE)

( * ) Notice: Subject to any disclaimer, the term of this patent is extended or adjusted under 35 U.S.C. 154(b) by 318 days.

(21) Appl. No.: 13/035,382

(22) Filed: Feb. 25, 2011

(65) Prior Publication Data

US 2011/0152596 A1 Jun. 23, 2011

Related U.S. Application Data

(62) Division of application No. 11/836,905, filed on Aug. 10, 2007, now Pat. No. 7,977,523.

(30) Foreign Application Priority Data

Aug. 29, 2006 (DE) .......................... 10 2006 040 432

(51) Int. Cl.
*C07C 1/20* (2006.01)
*C07C 1/24* (2006.01)

(52) U.S. Cl.
USPC ............................ 585/640; 585/638; 585/639

(58) Field of Classification Search
USPC ......................................... 585/638, 639, 640
See application file for complete search history.

(56) References Cited

U.S. PATENT DOCUMENTS

| | | | |
|---|---|---|---|
| 2,744,057 A | | 5/1956 | Emmett |
| 3,140,249 A | | 7/1964 | Plank et al. |
| 3,170,000 A | * | 2/1965 | Verdol ......................... 568/907 |
| 3,405,074 A | | 10/1968 | Mattox |
| 4,079,019 A | | 3/1978 | Scherzer et al. |
| 4,239,651 A | | 12/1980 | Alafandi et al. |
| 4,254,296 A | * | 3/1981 | Manara et al. ................ 585/640 |
| 4,668,648 A | | 5/1987 | Strack et al. |
| 4,873,391 A | * | 10/1989 | Inoue et al. ................... 585/639 |
| 5,171,920 A | * | 12/1992 | Chaumette et al. .......... 585/640 |
| 5,254,785 A | | 10/1993 | Rosenfeld et al. |
| 7,361,714 B2 | | 4/2008 | Grass et al. |
| 7,910,786 B2 | | 3/2011 | Winterberg et al. |
| 7,919,662 B2 | | 4/2011 | Winterberg et al. |
| 7,968,758 B2 | | 6/2011 | Winterberg et al. |
| 7,977,523 B2 | | 7/2011 | Zanthoff et al. |
| 2006/0041167 A1 | | 2/2006 | Grass et al. |
| 2008/0058569 A1 | * | 3/2008 | Winterberg et al. .......... 585/639 |
| 2008/0058572 A1 | | 3/2008 | Fernandez et al. |
| 2011/0118523 A1 | | 5/2011 | Winterberg et al. |
| 2011/0152596 A1 | | 6/2011 | Zanthoff et al. |
| 2011/0217552 A1 | | 9/2011 | Schulze-Isfort et al. |
| 2012/0142985 A1 | | 6/2012 | Winterberg et al. |

FOREIGN PATENT DOCUMENTS

| | | | | |
|---|---|---|---|---|
| EP | 0 589 557 A2 | | 3/1994 | |
| GB | 1249 079 | | 10/1971 | |
| GB | 1 355 060 | | 5/1974 | |
| JP | 6-72904 | | 3/1994 | |
| JP | 06-072904 | * | 3/1994 | ............. C07C 11/09 |
| WO | WO 02/10313 A2 | | 2/2002 | |

OTHER PUBLICATIONS

Clark, "Supported Catalysts" in Kirk-Othmer Encyclopedia of Chemical Technology, John Wiley & Sons, 2001, available on-line Nov. 15, 2002.*
Machine Translation of Gyoda, et al., JP 06-072904—accessed on-line Jan. 18, 2013.*
European Search Report (with English translation of category of cited documents) mailed Jan. 10, 2008.
U.S. Appl. No. 13/997,677, filed Jun. 25, 2013, Schulze-Isfort, et al.
U.S. Appl. No. 13/880,862, filed Jul. 3, 2013, Winterberg, et al.
U.S. Appl. No. 14/005,479, filed Sep. 16, 2013, Winterberg, et al.

* cited by examiner

*Primary Examiner* — In Suk Bullock
*Assistant Examiner* — Bradley Etherton
(74) *Attorney, Agent, or Firm* — Oblon, Spivak, McClelland, Maier & Neustadt, L.L.P.

(57) ABSTRACT

The present invention relates to a process for preparing a catalyst which, in a formal sense, comprises 0.1 to 20% by mass of alkali metal and/or alkaline earth metal oxide, 0.1 to 99% by mass of oxide and 0.1 to 99% by mass of silicon dioxide, which is characterized in that it aluminum comprises the steps of treating an aluminosilicate with an aqueous alkali metal and/or alkaline earth metal salt solution under acidic conditions and calcining the aluminosilicate treated with aqueous alkali metal and/or alkaline earth metal salt solution, and to a catalyst which is obtainable by this process and, in a formal sense, comprises alkali metal and/or alkaline earth metal oxide, aluminum oxide and silicon dioxide, which is characterized in that the catalyst, in a formal sense, has a content of alkali metal and/or alkaline earth metal oxides of 0.5 to 20% by mass, a content of aluminum oxide of 4 to 30% by mass and a content of silicon dioxide of 60 to 95% by mass, and to the use of this catalyst in a process for preparing isoolefins having 4 to 6 carbon atoms by catalytic gas phase cleavage of tertiary alcohols or alkyl tert-alkyl ethers.

28 Claims, No Drawings

CATALYST AND PROCESS FOR PREPARING ISOOLEFINS

The present invention relates to a catalyst for cleaving alkyl tert-alkyl ethers or tertiary alcohols to isoolefins and alcohol or water.

Isoolefins, for example isobutene, are important intermediates for the preparation of a multitude of organic compounds. Isobutene is, for example, a starting material for the preparation of butyl rubber, polyisobutylene, isobutene oligomers, branched $C_5$ aldehydes, $C_5$ carboxylic acids, $C_5$ alcohols and $C_5$ olefins. It is also used as an alkylating agent, especially for the synthesis of tert-butylaromatics, and as an intermediate for obtaining peroxides. In addition, isobutene can be used as a precursor for methacrylic acid and its esters.

In industrial streams, isoolefins are usually present together with other olefins and saturated hydrocarbons with the same number of carbon atoms. The isoolefins cannot be removed in an economically viable manner from these mixtures with physical separating methods alone.

For example, isobutene is present in typical industrial streams together with saturated and unsaturated $C_4$ hydrocarbons. Owing to the small boiling point difference and the small separating factor between isobutene and 1-butene, isobutene cannot be removed from these mixtures in an economically viable manner by distillation. Isobutene is therefore frequently obtained from industrial hydrocarbons by converting isobutene to a derivative which can be removed easily from the remaining hydrocarbon mixture, and by dissociating the isolated derivative back to isobutene and derivatizing agent.

Typically, isobutene is removed from $C_4$ cuts, for example the $C_4$ fraction of a steamcracker, as follows. After removal of the majority of the polyunsaturated hydrocarbons, mainly the butadiene, by extraction/extractive distillation or selective hydrogenation to give linear butenes, the remaining mixture (raffinate I or selectively hydrogenated crack-$C_4$) is reacted with alcohol or water. Isobutene forms methyl tert-butyl ether (MTBE) when methanol is used, ethyl tert-butyl ether (ETBE) when ethanol is used and tert-butanol (TBA) when water is used. After they have been removed, these derivatives can be cleaved to isobutene in a reversal of their formation.

The cleavage of alkyl tert-butyl ethers (ATBE) to the corresponding isoolefins and alcohols and the cleavage of tertiary alcohols to the corresponding isoolefins and water can be performed in the presence of acidic or basic catalysts in the liquid phase or gas/liquid mixed phase or in the pure gas phase.

The cleavage in the liquid phase or gas/liquid phase has the disadvantage that the products formed, dissolved in the liquid phase, can enter into side reactions more easily. For example, the isobutene formed in the cleavage of MTBE can form undesired $C_8$ and $C_{12}$ components as a result of acid-catalysed dimerization or oligomerization. The undesired $C_8$ components are mainly 2,4,4-trimethyl-1-pentene and 2,4,4-trimethyl-2-pentene. In addition, some of the methanol formed in the cleavage is converted to dimethyl ether with elimination of water particularly over basic catalysts. When the reaction is not performed under pressures above the saturation vapour pressure of the reaction mixture, in order to counteract these problems, an additional solvent is necessary.

In the gas phase, the formation of side reactions as a result of reaction of the cleavage products with themselves can be suppressed owing to their lower concentrations in comparison to the cleavage in the liquid phase. However, other side reactions can occur owing to the relatively high cleavage temperatures. In the gas phase cleavage, catalysts are therefore required which catalyse the cleavage of tertiary alkyl ethers or tertiary alcohols to isoolefin and alcohol or water with very high selectivity, but do not promote any side reactions, for example C—C cleavage or dehydrogenation and C—C coupling reactions or ether formation of the alcohols formed. Moreover, these catalysts should enable high space-time yields and have a long lifetime. In addition, cleavage of the reactant with maximum selectivity for the isoolefin formed at a pressure of greater than 0.3 MPa is desirable.

The catalysts described in the literature for the gas phase cleavage of alkyl tert-alkyl ethers (ATAE) and tertiary alcohols to the corresponding isoolefins and alcohol or water are a multitude of catalysts. This is true in particular for catalysts which are utilized for the cleavage of methyl tert-butyl ether (MTBE).

The catalysts used are usually metal oxides having an empirical formula of $M_aO_x$, mixed metal oxides with empirical formulae $M_aM_bM_nO_y$, especially those which contain M=Si or M=Al, acids on metal oxide supports or metal salts.

U.S. Pat. No. 4,254,290 describes, as cleavage catalysts, for example, $SiO_2/Al_2O_3$ or $WO_3/Al_2O_3$. U.S. Pat. No. 4,320,232 and U.S. Pat. No. 4,521,638 claim, for the cleavage of tertiary ethers, catalysts consisting of phosphoric acid on supports. Aluminium oxide on silica gel is utilized as a cleavage catalyst in U.S. Pat. No. 4,398,051. In the two patents U.S. Pat. No. 4,357,147 and U.S. Pat. No. 5,254,785, zeolites are used for the same purpose.

In JP 59010528, the cleavage catalyst used is sulphated titanium dioxide or zirconium dioxide. Ethers are cleaved in U.S. Pat. No. 5,607,992 by using a zirconium oxide/cerium oxide catalyst, in U.S. Pat. No. 6,124,232 by using zirconium oxide/tungsten oxide, in U.S. Pat. No. 6,162,757 by using a mixed oxide of zirconium and rare earths.

WO 2005-066101 claims a catalyst with the general empirical formula $X_mY_nZ_pO_q$ where X is at least one element of the fourth group of the Periodic Table of the Elements, Y is at least one metal from the third and/or sixth group and Z is at least one element from the seventh, eighth or eleventh group.

JP 1993-229965 claims a catalyst with the empirical formula $Si_aX_bY_cZ_dO_e$. (Here, Si and O in each case are silicon and oxygen; X is at least one element which is selected from the group consisting of titanium and zirconium; Y is an element which is selected from the group consisting of magnesium and calcium; Z is at least one element which is selected from the group consisting of sodium, potassium, chlorine and sulphur; a, b, c, d and e indicate the atomic ratio of the individual elements. When a=1, b=0.001 to 10, c=0.0001 to 5, d=0 to 1; e is the number of oxygen atoms needed to satisfy the valency of the individual constituents mentioned above.) U.S. Pat. No. 5,171,920 describes, in Example 4, the preparation of a cleavage catalyst which, in a formal sense, contains the components silicon dioxide, aluminium oxide and magnesium oxide. The preparation is done in such a way that silicon dioxide is first saturated/impregnated with an aqueous magnesium nitrate solution, and an intermediate drying is followed by a further saturation/impregnation with an aqueous aluminium nitrate solution. Subsequently, predrying is followed by calcination.

EP 0 589 557 claims, inter alia, a cleavage catalyst which consists, in a formal sense, of magnesium oxide, aluminium oxide and silicon dioxide. In its preparation, an aluminosilicate is impregnated in a first step with an aqueous magnesium salt solution in such a way that, during the impregnation, the pH of the impregnation solution can be adjusted to a pH of 7 to 11 by adding a base. In order to obtain particularly active and selective catalysts, impregnation times of over 200 h are required in some cases.

In the cleavage of alkyl tert-alkyl ethers or tertiary alcohols to isoolefin and alcohol, the known catalysts have one or more of the following disadvantages: low selectivity for the target products, use of high temperatures in the cleavage, in some cases above 500° C., short lifetimes of the catalysts, and complicated and hence costly preparation of the catalyst.

It is therefore an object of the invention to provide a cleavage catalyst which does not have one or more of these disadvantages.

It has now been found that, surprisingly, mixed oxide catalysts which consist, in a formal sense, of aluminium oxide, silicon dioxide and at least one oxide from the group of the alkali metal or alkaline earth metals, especially magnesium oxide, and which are preferably prepared by impregnating an aluminosilicate at least once with an acidic aqueous solution which contains at least one alkali metal and/or alkaline earth metal compound, and subsequent calcination, cleave alkyl tert-alkyl ethers (ATAE) and tertiary alcohols with very high selectivities to the corresponding isoolefins and have very long lifetimes. The impregnation can be effected, for example, by simply mixing the aluminosilicate with the acidic aqueous impregnation solution without any need for additional pH monitoring and without particularly long impregnation times being necessary. This finding is surprising, since EP 0 589 557 A2 explicitly points out that, during the impregnation, the pH in the supernatant solution has to be kept in the range of 7 to 11 by addition of bases, and that long impregnation times are required in order to obtain catalysts with high activity and low tendency to form by-products.

The present invention therefore provides a process for preparing a catalyst which, in a formal sense, comprises 0.1 to 20% by mass of alkali metal and/or alkaline earth metal oxide, 0.1 to 99% by mass of aluminium oxide and 0.1 to 99% by mass of silicon dioxide, which is characterized in that it comprises the steps of treating an aluminosilicate with an aqueous alkali metal and/or alkaline earth metal salt solution under acidic conditions and calcining the aluminosilicate impregnated with aqueous alkali metal and/or alkaline earth metal salt solution.

The present invention likewise provides a catalyst which, in a formal sense, comprises alkali metal and/or alkaline earth metal oxide, aluminium oxide and silicon dioxide, which is characterized in that the catalyst, in a formal sense, has a content of alkali metal and/or alkaline earth metal oxides of 0.5 to 20% by mass, a content of aluminium oxide of 4 to 30% by mass and a content of silicon dioxide of 60 to 95% by mass, and also a process for preparing isoolefins having 4 to 6 carbon atoms of the formula I

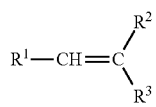

I by catalytic gas phase cleavage of a starting compound of the formula II

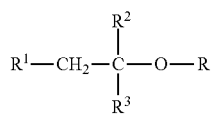

II to give a compound of the formula I and a compound of the formula III

R—OH    III where, in the formulae I to III, the R radical is H or an alkyl radical having 1 or 2 carbon atom(s), the $R^1$ radical is H or a methyl or ethyl radical, and the $R^2$ and $R^3$ radicals are each methyl or ethyl radicals, where the $R^2$ and $R^3$ radicals may be the same or different, at a temperature of 110 to 450° C. and a pressure of 0.1 to 2 MPa, which is characterized in that the catalyst used in the gas phase cleavage is an inventive catalyst or a catalyst prepared in accordance with the invention.

The preparation of isoolefins by gas phase cleavage of ATAE or tertiary alcohols using the inventive catalyst has several advantages: even in the case of conversions of the feedstocks of over 70%, the corresponding isoolefins are formed in selectivities of over 99%. In the case of cleavage of ATBE, the selectivities for the ethers formed from the eliminated alcohol are below 30%. The cleavage can be performed at temperatures, which are relatively low for cleavage reactions, of 150 to 450° C., preferably at temperatures of 230 to 350° C. The conversions can be performed at pressures of greater than 0.3 MPa, so that condensation of the isoolefins formed against cooling water is possible. The catalyst features a long lifetime. The catalyst does not contain any heavy metals, so that ecologically harmful substances occur neither in the course of its preparation nor in the course of its disposal. Variation of the content of alkaline earth metal oxide allows the activity to be adjusted optimally for each reactant.

The process according to the invention and the inventive catalysts are described by way of example below without any intention that the invention be restricted to these exemplary embodiments. When ranges, general formulae or compound classes are specified below, these are intended to encompass not only the corresponding ranges or groups of compounds which are mentioned explicitly but also all sub-regions or sub-groups of compounds which can be obtained by excluding individual values (ranges) or compounds.

The process according to the invention for preparing a catalyst which, in a formal sense, comprises 0.1 to 20% by mass of alkali metal and/or alkaline earth metal oxide, 0.1 to 99% by mass of aluminium oxide and 0.1 to 99% by mass of silicon dioxide, comprises the steps of
a) treating an aluminosilicate with an aqueous alkali metal and/or alkaline earth metal salt solution under acidic conditions and
b) calcining the aluminosilicate treated with aqueous alkali metal and/or alkaline earth metal salt solution.

Preference is given to preparing a catalyst which, in a formal sense, has a content of magnesium oxide of 0.5 to 20% by mass, a content of aluminium oxide of 4 to 30% by mass and a content of silicon dioxide of 60 to 95% by mass.

In the context of the present invention, aluminosilicates shall be understood to mean compounds which are composed, in a formal sense, essentially of contents of aluminium oxide ($Al_2O_3$) and silicon dioxide ($SiO_2$). The aluminosilicates used in the process according to the invention may have 1 to 99% by mass of silicon dioxide and 1 to 99% by mass of aluminium oxide ($Al_2O_3$). The inventive aluminosilicates may also contain small contents of alkali metal or alkaline earth metal oxides. In the process according to the invention, the aluminosilicates used may also be zeolites, for example zeolite A, X, Y, USY or ZSM-5, or amorphous zeolites (for example MCM 41 from Mobil Oil). The composition of the aluminosilicates used or of the resulting catalysts can be determined, for example, by classical analysis, fusion with borax and XFA (X-ray fluorescence analysis), energy-dispersive X-ray analysis, flame spectrometry (Al and Mg, not Si), wet digestion and subsequent ICP-OES (optical emission spectrometry with inductively coupled high-frequency plasma) or atomic absorption spectroscopy. Preference is given to determining the composition by fusion with borax and subsequent XFA or by wet digestion and subsequent ICP-OES.

The aluminosilicates used in the process according to the invention may be amorphous or crystalline. Suitable commercial aluminosilicates which can be used as starting materials in the process according to the invention are, for example, aluminosilicates which have been prepared by precipitation, gelation or pyrolysis.

In the process according to the invention, preference is given to using aluminosilicates which have 5 to 40% by mass, preferably 10 to 35% by mass, of aluminium oxide, and 60 to 95% by mass, preferably 65 to 90 mass, of silicon dioxide (based on the dry mass; treatment: calcination at 850° C. for 1 h). A particularly preferred aluminosilicate which can be used in the process according to the invention has a formal content of $Al_2O_3$ of 10 to 15% by mass and a content of silicon dioxide of 73 to 78% by mass. Such an aluminosilicate is supplied by Grace Davison under the name Davicat O 701.

The aluminosilicate can be used in the process according to the invention in a wide variety of different forms. For instance, the aluminosilicate can be used in the form of shaped bodies, for example tablets, pellets, granule, strands or extrudates. The aluminosilicate can also be used in the form of aluminosilicate powder. The starting material used may be powders with different mean particle size and different particle size distribution. In the process according to the invention, preference is given to using an aluminosilicate powder in which 95% of the particles have a mean particle size of 5 to 100 µm, preferably 10 to 30 µm and more preferably 20 to 30 µm. The particle size can be determined, for example, by laser diffraction with a particle analyser from Malvern, for example the Mastersizer 2000.

Process Step a)

In step a), an alkali metal salt solution and/or an alkaline earth metal salt solution can be used. It is also possible in step a) to use a salt solution which comprises one or more salts of alkali metals and of alkaline earth metals. To prepare the aqueous salt solutions, alkali metal and/or alkaline earth metal compounds which are water-soluble or are converted to water-soluble compounds by adding an acid may be used. The salts used are preferably the nitrates of the alkali metals or alkaline earth metals.

The acidic aqueous alkali metal and/or alkaline earth metal salt solution used preferably has a pH of less than 6, preferably of less than 6 to 3 and more preferably of 5.5 to 3.5. The pH can be determined, for example, with the aid of a glass electrode or indicator paper. When the salt solution has a pH which is greater than or equal to 6, the pH can be adjusted by adding an acid, preferably the acid whose alkali metal and/or alkaline earth metal salt is present in the solution. When the alkali metal and/or alkaline earth metal salt solution comprises the nitrates as salts, preference is given to using nitric acid as the acid.

The alkali metal salt solution used in the process according to the invention is preferably a magnesium or calcium salt solution. Preference is given to using magnesium salt solutions which, as magnesium salts, comprise the salts of strong mineral acids, for example magnesium nitrate hexahydrate or magnesium sulphate heptahydrate. The calcium salt used may, for example, be calcium nitrate tetrahydrate. In the process according to the invention, preference is given to using a magnesium salt solution and particular preference to using a magnesium nitrate (hexahydrate) solution.

When the alkali metal and/or alkaline earth metal salt solution used in step a) comprises a magnesium salt, the magnesium content of the solution is preferably 0.1 to 3 mol/l, preferably 0.5 to 2.5 mol/l.

The treatment in step a) can be effected in various ways which are suitable for contacting the aluminosilicate with the alkali metal and/or alkaline earth metal salt solution. Possible treatment methods are, for example, impregnation, saturation, spraying or immersing the aluminosilicate with the alkali metal and/or alkaline earth metal salt solution. It may be advantageous when the treatment of the aluminosilicate is effected in such a way that the alkali metal and/or alkaline earth metal salt solution can act on the aluminosilicate for at least 0.1 to 5 h, preferably 0.5 to 2 h. Such an action time may be advantageous especially when the treatment is effected by simple saturation.

In a preferred embodiment of the inventive step a) of the process according to the invention, the treatment of aluminosilicate, especially aluminosilicate shaped bodies, with the alkali metal and/or alkaline earth metal salt solution can be effected, for example, by vacuum impregnation in a vacuum impregnation unit suitable therefor. In this type of treatment, the aluminosilicate in the vacuum impregnation unit is first evacuated. Subsequently, the alkali metal and/or alkaline earth metal salt solution is sucked in up to above the upper edge of the support bed, so that the entire aluminosilicate is covered with the solution. After an action time which is preferably 0.1 to 10 h, preferentially 0.5 to 2 h, the solution which has not been taken up by the support is discharged.

In a further preferred embodiment of the inventive step a) of the process according to the invention, the treatment of aluminosilicate, especially aluminosilicate shaped bodies, with the alkali metal and/or alkaline earth metal salt solution can be effected, for example, by spraying or immersing the aluminosilicate. The spraying or immersion of the aluminosilicate with the alkali metal and/or alkaline earth metal salt solution is preferably effected by spraying or pouring the solution onto the aluminosilicate rotating in a drum. The treatment can be effected in one step, i.e. the entire amount of alkali metal and/or alkaline earth metal salt solution is added at the start to the aluminosilicate in one step. However, the salt solution can also be metered in by spraying or immersion in small portions, the period of addition being preferably 0.1 to 10 h and preferentially 1 to 3 h. The amount of salt solution is preferably such that the entire solution of the aluminosilicate is taken up.

Saturation in particular, but also spraying or immersion, can be performed in customary industrial apparatus, for example conical mixers or intensive mixers, as supplied, for example, by Eirich.

The treatment of the aluminosilicate with the alkali metal and/or alkaline earth metal salt solution in step a) can be effected in one step or in a plurality of partial steps. In particular, it is possible to perform the treatment in two or more partial steps. In each of the individual partial steps, the same alkali metal and/or alkaline earth metal salt solution can be used in each case, or else an alkali metal and/or alkaline earth metal salt solution of different concentration and/or composition can be used in each partial step. For example, initially only a portion of the alkali metal and/or alkaline earth metal salt solution can be added to the aluminosilicate and, optionally after intermediate drying, the remaining amount of the salt solution used can be added at the same temperature or a different temperature. However, it is also possible to treat the aluminosilicate with different alkali metal and/or alkaline earth metal salt solutions (different concentration and/or composition) at the same or a different temperature. It is not only possible that step a) is performed in two or more substeps. It is likewise possible that the process has a plurality of steps a). In this case too, identical or different alkali metal and/or alkaline earth metal salt solutions in relation to concentration and/or composition can be used in the different steps a).

The treatment in step a) can be performed preferably at a temperature of 10 to 120° C., preferentially of 10 to 90° C., more preferably of 15 to 60° C. and most preferably at a temperature of 20 to 40° C.

It may be advantageous when one or more additives is/are added or admixed to the aluminosilicate or to the alkali metal and/or alkaline earth metal salt solution in step a). Such additives may, for example, be binders, lubricants or shaping assistants. A suitable binder may, for example, be boehmite or pesudoboehmite, as supplied, for example, under the name Disperal (boehmite having a formal $Al_2O_3$ content of approx. 77% by mass) by Sasol Deutschland GmbH. When boehmite, especially Disperal, is added as a binder, it is preferably added as a gel which can be obtained, for example, by stirring 197 parts by mass of Disperal into 803 parts by mass of 1.28% by mass aqueous nitric acid, stirring thoroughly at 60° C. for 3 h, cooling to room temperature and replacing any evaporated water. The shaping assistants used may, for example, be silicas, especially pyrogenic silicas, as sold, for example, by Degussa AG under the name Aerosil, bentonites, clays, kaolin, kaolinite, ball clay and other substances familiar for this purpose to those skilled in the art. The lubricants added, whose use may be advantageous for improved tabletting, may, for example, be graphite.

One or more of the abovementioned additives may be added in step a) in various ways. In particular, the addition can be effected during the treatment of the aluminosilicate with the alkali metal and/or alkaline earth metal salt solution. For example, aluminosilicate, additive and alkali metal and/or alkaline earth metal salt solution can be charged into an industrial apparatus and then mixed intimately. Another possibility is to first mix the aluminosilicate with the additive and then to add the alkali metal and/or alkaline earth metal salt solution. In a further variant, additive and alkali metal and/or alkaline earth metal salt solution can be metered simultaneously to the aluminosilicate. The addition can be effected in each case in one batch, in portions or by spraying. The addition time is preferably less than 5 h, preferentially less than 3 h. It may be advantageous to continue to mix the mixture for 0.1 to 10 h, preferably for 0.5 to 3 h.

Process Step b):

The process according to the invention has at least one process step b) in which the aluminosilicate treated with alkali metal and/or alkaline earth metal salt solution is calcined. The calcination is effected preferably in a gas stream, for example in a gas stream which comprises, for example, air, nitrogen, carbon dioxide and/or one or more noble gases, or consists of one or more of these components. Preference is given to effecting the calcining using air as the gas stream.

The calcination in the inventive process step b) is performed preferably at a temperature of 200 to 1000° C., preferably of 300 to 800° C. The calcination is effected preferably for a time of 0.1 to 10 hours, preferably 1 to 5 hours. Particular preference is given to performing the calcination at a temperature of 200 to 1000° C., preferably 300 to 800° C., for 0.1 to 10 hours, preferably 1 to 5 hours.

The industrial calcination can preferably be performed in a shaft oven. However, the calcination can also be performed in other known industrial apparatus, for example fluidized bed calciners, rotary tube ovens or tray ovens.

Process Step c):

It may be advantageous when a step c), in which the aluminosilicate treated with alkali metal and/or alkaline earth metal salt solution is dried, is performed between steps a) and b). The drying in step c) can be effected at a temperature of 100 to 140° C. The drying is preferably effected in a gas stream. The drying can be performed, for example, in a gas stream which comprises, for example, air, nitrogen, carbon dioxide and/or one or more noble gases, or consists of one or more of these components. The intermediate drying step after the treatment with alkali metal and/or alkaline earth metal salt solution and before the calcining can achieve the effect that no large amounts of steam are released in the course of calcination. In addition, the drying can prevent water which evaporates spontaneously in the course of calcining from destroying the shape of the catalyst.

Depending on the desired shape in which the catalyst is to be present, it may be advantageous to adjust the preparation process appropriately by additional process steps.

When, for example, pulverulent catalyst is to be prepared by the process according to the invention, the aluminosilicate can be used in the form of aluminosilicate powder and, for example, treated with the alkali metal and/or alkaline earth metal salt solution (for example by impregnation), for example in a conical mixer, optionally dried and then calcined. However, a pulverulent catalyst can also be prepared by processing a shaped catalyst body to give a pulverulent catalyst by grinding and screening.

The shaped catalyst bodies may be present, for example, in the form of extrudates, spheres, pellets or tablets. In order to arrive at the shaped catalyst (shaped catalyst bodies), depending on the particular shaping variant, it is possible to perform further process steps, for example shaping, grinding or screening, in addition to the process steps of treatment, drying, calcination. Shaping assistants can be introduced at various points in the process. The shaped catalyst bodies can be prepared in various ways:

In a first variant, shaped catalyst bodies, especially inventive shaped catalyst bodies, can be obtained by treating shaped aluminosilicate bodies with an aqueous alkali metal and/or alkaline earth metal salt solution, optionally drying and then calcining.

In a second embodiment, a shaped catalyst body, especially an inventive shaped catalyst body, can be obtained by first treating an aluminosilicate powder with an acidic aqueous alkali metal and/or alkaline earth metal salt solution, then optionally drying and subsequently calcining it, and subsequently processing the resulting catalyst powder by processes customary in industry, for example compaction, extrusion, pelletization, tabletting, granulation or coating to give shaped catalyst bodies. Additives required for the shaping, for example binders or further assistants, can be added at various points in the preparation process, for example in process step a). When a shaped body is prepared from an aluminosilicate powder as a starting material, it is possible to start from powders with different mean particle size and different particle size distribution. For the preparation of shaped bodies, preference is given to using an aluminosilicate powder in which 95% of the particles have a particle size of 5 to 100 µm, preferably 10 to 30 µm and more preferably 20 to 30 µm (determined by laser diffraction; see above).

In a third embodiment of the process according to the invention, pellets of the catalyst, especially of the inventive catalyst, can be obtained by, in process step a), treating an aluminosilicate powder with an aqueous acidic alkali metal and/or alkaline earth metal salt solution, optionally drying (process step c)) and then calcining in process b), and pelletizing the catalyst powder thus obtained with addition of binder, for example in an Eirich mixer, and drying the resulting pellets in a further process step c) and then calcining them in a further process step b).

In a fourth embodiment of the process according to the invention, pellets of the catalyst, especially of the inventive catalyst, can be obtained by, in process step a), mixing an aluminosilicate powder, binder and acidic aqueous alkali metal and/or alkaline earth metal salt solution, and pelletizing the aluminosilicate powder thus treated, for example in an Eirich mixer, and drying the resulting moist pellets in process step c) and then calcining them in a gas stream in process step b).

In a fifth embodiment of the process according to the invention, tablets of the catalyst, especially of the inventive catalyst, can be obtained by, in process step a), mixing an aluminosilicate powder, binder, optionally lubricant and acidic aqueous alkali metal and/or alkaline earth metal salt solution, and pelletizing the aluminosilicate powder thus treated, for example in an Eirich mixer, to give micropellets, preferably having a mean diameter of 0.5 to 10 mm, preferably 1 to 5 mm and more preferably of 1 to 3 mm (the particle size can be determined, for example, by screen analysis), and drying the resulting moist pellets in process step c) and then optionally calcining them in a gas stream in process step b). The resulting pellets may then, unless already done in process step a), be mixed with a lubricant, for example graphite, and then tabletted on a commercial tabletting press, for example a rotary tabletting press. The tablets may then, if process step b) is yet to be performed, be calcined in process step b), or optionally post-calcined.

In a sixth embodiment of the process according to the invention, tablets of the catalyst, especially of the inventive catalyst, can be obtained by grinding preshaped shaped catalyst bodies, as can be obtained, for example, as pellets in embodiment three or four, and screening the granule/powder obtained, so as to obtain a tablettable granule of catalyst, and adding lubricants to this granule. The granule thus prepared can then be tabletted. The tablets may then, if process step b) is yet to be performed, be calcined in process step b). The addition of a lubricant can be dispensed with when a lubricant has already been added in the course of preparation of the pellets, for example in process step a).

In a seventh embodiment of the process according to the invention, materials/supports coated with the catalyst, especially with the inventive catalyst, can be prepared. In this embodiment, a catalyst powder is first prepared by, in process a), treating an aluminosilicate powder with an acidic aqueous alkali metal and/or alkaline earth metal salt solution, optionally drying (process step c)) and optionally calcining (process step b)). The catalyst powder thus obtained is then suspended in a suspension medium, for example water or alcohol, for which a binder can optionally be added to the suspension. The suspension thus prepared can then be applied to any material. The application is followed by optional drying (process step c)) and then calcining (process step b)). In this way, materials/supports coated with the catalyst, especially with the inventive catalyst, can be provided. Such materials/supports may, for example, be metal plates or fabric, as can be used as internals in reactors or columns, especially reactive distillation columns, or else metal, glass or ceramic spheres, or spheres of inorganic oxides.

In an eighth embodiment of the process according to the invention, extrudates of the catalyst, especially of the inventive catalyst, can be obtained by, in process step a), mixing an aluminosilicate powder, acidic aqueous alkali metal and/or alkali metal salt solution, binder, for example Disperal, and further shaping assistants customary for extrusion, for example clays such as bentonite or attapulgite, in a kneader or Eirich mixer, and extruding them in an extruder to give extrudates, preferably having a mean diameter of 0.5 to 10 mm, preferentially of 1 to 5 mm and more preferably of 1 to 3 mm, and drying the resulting moist extrudates optionally in process step c) and then calcining them in a gas stream in process step b).

The catalysts obtainable by the process according to the invention are especially those which consist, in a formal sense, of aluminium oxide ($Al_2O_3$) and silicon dioxide ($SiO_2$) and at least one oxide from the group of alkali metal and alkaline earth metal oxides. The average mass fraction of aluminium oxide in these catalysts is preferably 1 to 99% by weight, that of silicon dioxide preferably 1 to 99% by weight and the mass fraction of the alkali metal and alkaline earth metal oxides in total preferably 0.1 to 30% by weight. Such catalysts preferably have magnesium as the alkaline earth metal, in particular as the sole alkaline earth metal.

The inventive catalyst which, in a formal sense, comprises alkali metal and/or alkaline earth metal oxide, aluminium oxide and silicon dioxide features, in a formal sense, a content of alkali metal and/or alkaline earth metal oxides (total of the alkali metal and/or alkaline earth metal oxides present in the catalyst) of 0.5 to 20% by mass, a content of aluminium oxide ($Al_2O_3$) of 4 to 30% by mass and a content of silicon dioxide of 60 to 95% by mass. The inventive catalyst may, for example, be obtained by the above-described process according to the invention.

The inventive catalyst preferably contains an alkaline earth metal oxide, preferably magnesium oxide. The inventive catalyst more preferably contains magnesium oxide as the sole alkaline earth metal oxide. It may be advantageous when the catalyst comprises an alkali metal oxide in addition to the alkaline earth metal oxide. This may, for example, be selected from $Na_2O$ or $K_2O$. The inventive catalyst preferably comprises $Na_2O$ as the alkali metal oxide.

When the inventive catalyst comprises magnesium oxide, it preferably has a content of magnesium oxide of 0.5 to 20% by mass, preferably of 5 to 15% by mass and more preferably of 10 to 15% by mass, and a content of aluminium oxide of 4 to 30% by mass, preferably of 10 to 20% by mass, and a content of silicon dioxide of 60 to 95% by mass, preferably of 70 to 90% by mass.

The inventive catalyst preferably has a BET surface area (determined by volumetric means with nitrogen to DIN ISO 9277) of 200 to 450 $m^2/g$, preferably of 200 to 350 $m^2/g$. When the inventive catalyst is applied as an active composition on a support, only the active composition has a BET surface area in the range specified. The material composed of catalyst and support may, in contrast, depending on the properties of the support, have a significantly different BET surface area, especially a smaller BET surface area. The pore volume of the inventive catalyst is preferably 0.5 to 1.3 ml/g, preferentially 0.65 to 1.1 ml/g. The pore volume is preferably determined by the cyclohexane method.

In this method, the sample to be tested is first dried at 110° C. to constant weight. Subsequently, approx. 50 ml of the sample weighed accurately to 0.01 g are introduced into a cleaned impregnation tube dried to constant weight, which has an outlet orifice with a ground-glass tap at the lower end. The outlet orifice is covered with a small piece of polyethylene, which prevents blockage of the outlet orifice by the sample. After the impregnation tube has been filled with the sample, the tube is carefully sealed air-tight. Subsequently, the impregnation tube is connected to a water-jet pump, the ground-glass tap is opened and the water jet is used to establish a vacuum in the impregnation tube of 20 mbar. The vacuum can be checked on a parallel vacuum meter. After 20 min, the ground-glass tap is opened and the evacuated impregnation tube is subsequently connected to a cyclohexane receiver in which an accurately measured volume of cyclohexane is initially charged, such that opening of the ground-glass tap results in suction of cyclohexane from the receiver into the impregnation tube. The ground-glass tap remains open until the entire sample has been flooded with cyclohexane. Subsequently, the ground-glass tap is closed again. After 15 min, the impregnation tube is aerated cautiously and the unabsorbed cyclohexane is discharged into the receiver. Cyclohexane adhering in the impregnation tube or in the outlet orifice or the connection to the cyclohexane receiver can be conveyed via the aeration line into the receiver by a single cautious pressure impulse from a suction ball. The volume of the cyclohexane present in the receiver is noted. The pore volume is determined from the absorbed volume of cyclohexane, which is determined from the cyclohexane volume in the receiver before the measurement minus the cyclohexane volume in the receiver after the measurement, divided by the mass of the sample analysed.

The mean pore diameter (preferably determined on the basis of DIN 66133) of the inventive catalyst is preferably 5 to 20 nm, preferably 8 to 15 nm. More preferably, at least 50%, preferably over 70%, of the total pore volume (sum of the pore volume of the pores having a pore diameter of greater than or equal to 3.5 nm determined by mercury porosimetry to DIN 66133) of the catalyst is accounted for by pores having a diameter of 3.5 to 50 nm (mesopores).

The inventive catalysts may have different dimensions, especially a dimension of 10 µm to 10 mm. For use of the catalysts in a fluidized bed reactor, the mean particle size (determined by means of laser diffraction on a Mastersizer 2000 from Malvern) of the catalyst is preferably 10 to 200 µm, preferentially 50 to 150 µm. For the use of the catalyst in fixed bed reactors, it is preferably present in the form of a shaped body, for example as a strand, pellet, tablet, sphere or granule, and preferably has dimensions (longest dimension or diameter) of 0.5 to 10 mm, preferably of 1 to 5 mm.

The inventive catalyst may also be applied on a support, for example a metal, plastic or ceramic support, preferably on a support which is inert in relation to the reaction in which the catalyst is to be used. In particular, the inventive catalyst may also be applied to a metal support, for example a metal plate or a metal fabric. Such supports provided with the inventive catalyst may be used, for example, as internals in reactors or reactive distillation columns. The supports may also be metal, glass or cereamic spheres or spheres of inorganic oxides. When the inventive catalyst is applied on an inert support, the mass and composition of the inert support is not taken into account in the determination of the composition of the catalyst.

The inventive catalyst or a catalyst prepared by the process according to the invention can be used as a catalyst for numerous reactions. In particular, the inventive catalyst or a catalyst prepared by the process according to the invention can be used in a process for preparing isoolefins having 4 to 6 carbon atoms of the formula I

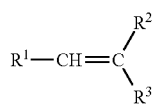

by catalytic gas phase cleavage of a starting compound of the formula II

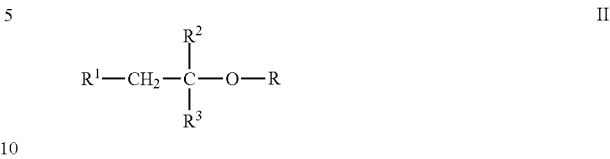

to give a compound of the formula I and a compound of the formula III

where, in the formulae I to III, the R radical is H or an alkyl radical having 1 or 2 carbon atom(s), the $R^1$ radical is H or a methyl or ethyl radical, and the $R^2$ and $R^3$ radicals are each methyl or ethyl radicals, where the $R^2$ and $R^3$ radicals may be the same or different, at a temperature of 110 to 450° C. and a pressure of 0.1 to 2 MPa.

The compounds of the formula II used may, for example, be tertiary alcohols having from 4 to 6 carbon atoms. In such a process according to the invention, the compound II cleaved is preferably tert-butanol (TBA) to isobutene as the compound of the formula I and water as the compound III.

The TBA which can be used in the cleavage process can stem from various industrial processes. One of the most important is the reaction of isobutenic $C_4$ hydrocarbon mixtures with water. Processes for preparing TBA are published, for example, in the patents DE 103 30 710 and U.S. Pat. No. 7,002,050. TBA can be used in pure form, as a TBA/water azeotrope or as another TBA-water mixture.

In a cleavage process according to the invention, preference is given to cleaving a compound of the formula II in which R is a methyl, ethyl or propyl radical. Alkyl tert-alkyl ethers which can be used in the cleavage process according to the invention are, for example, methyl tert-butyl ether, ethyl tert-butyl ether or tert-amyl methyl ether (TAME). In the case of the inventive use of the inventive catalyst or of the catalyst prepared in accordance with the invention, particular preference is given to cleaving methyl tert-butyl ether to isobutene and methanol or ethyl tert-butyl ether to isobutene and ethanol.

In the cleavage process according to the invention, it is possible to use ATAEs which may stem from a wide variety of different processes. One process for preparing MTBE is described, for example, in DE 101 02 062. Processes for preparing ETBE are published, for example, in DE 10 2005 062700, DE 10 2005 062722, DE 10 2005 062699 or DE 10 2006 003492.

The inventive cleavage in the gas phase over the inventive catalyst is performed preferably at a temperature of 150 to 400° C. When the starting material used is MTBE, the cleavage of MTBE to isobutene and methanol is preferably performed at a temperature of 180 to 400° C., more preferably of 230 to 350° C.

The cleavage process according to the invention is preferably at a reaction pressure of 0.1 to 1 MPa. When isobutene is a product, it may be advantageous to perform the cleavage process according to the invention at a pressure of 0.2 to 1 MPa, preferably of 0.5 to 0.8 MPa. This is advantageous especially because isobutene can be condensed against cooling water at these pressures.

The specific catalyst hourly space velocity (WHSV; grams of reactant at room temperature per gram of catalyst per hour) in the cleavage process according to the invention is preferably 0.1 to 100 $h^{-1}$, preferably 0.5 to 30 $h^{-1}$. When the starting material used is MTBE, the cleavage of MTBE to isobutene and methanol is preferably performed at a WHSV of 0.1 to 100 h$^{-1}$, more preferably of 0.25 to 25 h$^{-1}$.

In order to minimize the workup complexity of the cleavage product mixture, high conversions for straight pass are preferably pursued. The process according to the invention is preferably performed in such a way that the conversions of compounds to be cleaved are over 70%, preferably over 80% and more preferably over 90% to 100%. When the reactants contain troublesome secondary components, it may be appropriate to restrict the conversion. When, for example, the feedstock mixture also contains 2-methoxybutane in addition to the MTBE to be cleaved, it may be necessary to reduce the conversion in straight pass in order not to exceed a defined ratio of linear butenes to isobutene in the reaction mixture. It may thus be advantageous to restrict the permissible conversion of MTBE the higher the content of 2-methoxybutane is in the feedstock mixture comprising MTBE. The restriction of the conversion can be achieved, for example, by increasing the WHSV and/or lowering the reaction temperature.

The selectivity of isoolefin formation in the process according to the invention is preferably over 98%, preferentially over 99%. The selectivity for the formation of alcohols in the process according to the invention in the case of ATAE cleavage, especially in the case of ATBE cleavage, is over 95%, especially over 99%.

The cleavage product mixture can be worked up by known industrial processes. Unconverted reactant can be recycled into the cleavage, optionally after partial discharge or purification.

The isoolefins obtained may be utilized as described in the introduction. Isobutene prepared by the cleavage process according to the invention can be used in particular for the preparation of butyl rubber, polyisobutylene, isobutene oligomers, branched $C_5$ aldehydes, $C_5$ carboxylic acids, $C_5$ alcohols, $C_5$ olefins, tert-butylaromatics and methacrylic acid and esters thereof.

The alcohols obtained in the cleavage of ATAE can be used again after processing, for example for the synthesis of ATAE.

The examples which follow are intended to illustrate the inventive catalyst and the process using the inventive catalyst without restricting the scope of application which is evident from the description and the claims.

EXAMPLE 1

Preparation of a Shaped Aluminosilicate Body 500 g of aluminosilicate powder (manufacturer: Grace Davison, Type: Davicat O 701, formal $Al_2O_3$ content: 13% by mass, formal $SiO_2$ content: 76% by mass, formal $Na_2O$ content: 0.1% by mass, ignition loss at 850° C.: approx. 11%), 363 g of Disperal gel (formal $Al_2O_3$ content: 15.6%), which is obtained by stirring 197 g of Disperal, a boehmite having a formal $Al_2O_3$ content of 77% by mass from Sasol Deutschland GmbH, into 803 g of 1.28% by mass aqueous nitric acid, subsequently stirring thoroughly, in the course of which the gel which forms is sheared constantly and thus kept in a free-flowing state, in a covered vessel at 60° C. for 3 h, cooling the gel to room temperature and replacement of any evaporated water, and 370 g of demineralized water (DM water) were initially mixed thoroughly with one another in an intensive mixer from Eirich. Subsequently, the mixture was pelletized in the intensive mixer from Eirich, to obtain uniformly round pellets with a diameter of approx. 1 to 3 mm within 30-40 minutes. The moist pellets were first dried in an air stream at 120° C. and then heated at 2 K/min to 550° C. and calcined in an air stream at this temperature for 10 h. The aluminosilicate pellets thus prepared contained, in a formal sense, 76% by mass of $Al_2O_3$ and 24% by mass of $SiO_2$. In addition, the catalyst prepared contained 0.12% by mass of sodium compounds (calculated as sodium oxide). The composition of the aluminosilicate pellets was calculated from the amount and the composition of the starting substances. The aluminosilicate pellets had a pore volume, determined by the above-described cyclohexane method, of 1.15 ml/g.

EXAMPLE 2

Preparation of a Shaped Catalyst (According to the Invention)

An impregnation solution having a magnesium content of 4.7% by mass was prepared from DM water and magnesium nitrate hexahydrate. The pH of this solution was 5.1. By means of vacuum impregnation, a screened-out fraction of the aluminosilicate support prepared in Example 1 (diameter: 1.0 mm-2.8 mm) was impregnated with the acidic magnesium nitrate solution. To this end, the pellets were introduced into a glass tube which was evacuated for about 30 min (water-jet pump vacuum of approx. 25 hPa). Subsequently, the impregnation solution was sucked in from the bottom up to above the upper edge of the solid-state bed. After an action time of about 15 minutes, the solution which had not been taken up by the support was discharged. The moist pellets were first dried to constant weight in an airstream at 140° C. and then heated to 450° C. at 3 K/min and calcined at this temperature for 12 h. The catalyst prepared consisted, in a formal sense, of 68% by mass of silicon dioxide, of 21% by mass of aluminium oxide and of 11% by mass of magnesium oxide. In addition, the catalyst prepared contained 0.11% by mass of sodium compounds (calculated as sodium oxide). The composition of the catalyst was calculated from the amount and the composition of the starting substances, and the impregnation solution which had run off. The amounts of sodium were part of the aluminosilicate used in Example 1. The pore volume, determined by the above-described cyclohexane method, was 1.1 ml/g.

EXAMPLE 3

Preparation of a Pulverulent $MgO/Al_2O_3/SiO_2$ Catalyst (by Impregnation of an Aluminosilicate with a Magnesium Salt Solution)

500 g of an aluminosilicate powder (manufacturer: Grace Davison, type: Davicat O 701, $Al_2O_3$ content: 13% by weight, $SiO_2$ content: 76% by weight, $Na_2O$ content: 0.1% by weight, ignition loss at 850° C.: 11%, particle size $d_{50}$=20 µm, determined by means of laser diffraction on a Mastersizer 2000 from Malvern) with a pore volume of 1.1 ml/g were mixed in a conical mixer with 550 ml of an acidic magnesium nitrate solution (Mg content: 4.7% by mass, pH=5.1) and mixed for 20 minutes. The moist powder was then first dried to constant weight at 140° C. in an airstream in a fluidized bed oven and then calcined at 450° C. in a muffle furnace for 10 h. The content of the main components calculated from the starting compounds (based on these main components) in the catalyst calcined at 850° C. was 12% by mass of $Al_2O_3$, 77% by mass of $SiO_2$, 11% by mass of MgO.

EXAMPLE 4

Preparation of Catalyst Tablets 645 g of magnesium nitrate hexahydrate were dissolved in 355 g of DM water. The pH of this solution was 3.5. 500 g of Disperal gel (formal $Al_2O_3$ content: 15.6% by weight) were stirred into this solution. The resulting viscous, but still readily stirrable and pumpable, suspension was then premixed directly with 917 g of aluminosilicate powder (manufacturer: Grace Davison, type: Davicat O 701, $Al_2O_3$ content: 13% by weight, $SiO_2$ content: 76% by weight, $Na_2O$ content: 0.1% by weight, ignition loss at 850° C.: 11%, particle size $d_{50}$=20 μm, determined by means of laser diffraction on a Mastersizer 2000 from Malvern) and 42 g of graphite (manufacturer: Edelgraphitgesellschaft Bonn, type: K 16) as tabletting assistants. This afforded a mass which consists of loose, slightly moist agglomerates. This mass was then pelletized in an intensive mixer from Eirich. In order to obtain tablettable granule, the pelletization was controlled in such a way that predominantly rounded pellets having a diameter of less than 1 mm were formed. The moist pellets were then initially dried at 140° C. for 2 h and then calcined at 450° C. in a rotary tube flowed through by air for 1 h.

The calcined pellets were then compressed with a tabletting press (from Ronchi) to give tablets having a diameter of 3 mm and a height of 4 mm. Subsequently, the tablets were post-calcined at 560° C. for 2 hours. The nominal content in the tablet of $Al_2O_3$ was 19.7 parts by mass, that of $SiO_2$ 70.8 parts by mass, that of MgO 10.0 parts by mass, that of $Na_2O$ 0.1 part by mass. The tablets had a BET surface area (to DIN ISO 9277) of 253 m²/g. The total pore volume determined by means of mercury porosimetry on the basis of DIN 66133 (maximum measurement pressure: 400 MPa) for pores having a diameter of 3.5 to 10 000 nm was 0.68 ml/g. The macropore volume (pores having a diameter of 50-10 000 nm) was 0.1 ml/g (macropore content 15%) and the mesopore volume (pores with diameter of 3.5 to 50 nm) was 0.57 ml/g (mesopore content 85%). The mean pore diameter was 9.6 nm.

EXAMPLE 5

Gas Phase Cleavage of MTBE to Isobutene and Methanol (in Accordance with the Invention)

The cleavage was performed in a tubular reactor with a heating jacket through which a heat carrier oil (Marlotherm SH from Sasol Olefins & Surfactants GmbH) flowed. The catalyst used was the catalyst prepared in Example 2. The reactant used was industrial MTBE (Driveron from Oxeno Olefinchemie GmbH) having a purity of 99.7% by mass.

Before entry into the reactor, the MTBE was evaporated fully in an evaporator at 250° C. At a temperature of 250° C. (temperature of the Marlotherm in the feed of the reactor jacket) and a pressure of 7 $bar_{absolute}$ (bara), 500 g per hour of MTBE were passed through 282 g of catalyst, corresponding to a WHSV of 1.77 h$^{-1}$. The gaseous cleavage product mixture was partly condensed in a condenser. The resulting liquid phase was weighed and the volume of the gas phase was measured. The two phases were analysed by gas chromatography.

The cleavage was performed under the above conditions over a period of more than 2500 hours. The isobutene conversions, the selectivities of isobutene formation (number of moles of isobutene formed relative to number of moles of MTBE converted) and the selectivities of methanol formation (number of moles of methanol formed relative to number of moles of isobutene converted) were calculated at various reaction times from the composition of the cleavage product mixture, the reactant mass and the mass of the cleavage product mixture. The resulting values were compiled in Table 1 below.

TABLE 1

Conversion and selectivities of the cleavage of MTBE in Example 5

| | Experimental duration (h) | | | | | | |
|---|---|---|---|---|---|---|---|
| | 51 | 99 | 495 | 1000 | 1511 | 1992 | 2497 |
| MTBE conversion (%) | 85.4 | 84.2 | 81.1 | 77.3 | 76.2 | 73.6 | 72.5 |
| Isobutene selectivity (%) | 99.98 | 99.98 | 99.97 | 99.97 | 99.97 | 99.97 | 99.97 |
| Methanol selectivity (%) | 97.1 | 97.4 | 97.8 | 97.8 | 97.7 | 97.8 | 97.7 |

The experiment shows that the inventive catalyst is very suitable for the cleavage of MTBE to isobutene and methanol. The selectivities both of isobutene formation and of methanol formation were excellent and remained virtually constant over the entire experimental duration. The activity of the catalyst decreased with increasing experimental duration. However, after approx. 2500 hours, it was still 85% of the activity of the catalyst after 50 h of experimental duration, so that it was possible to assume a lifetime of the catalyst of well over one year in an industrial production plant.

EXAMPLE 6

Gas Phase Cleavage of MTBE to Isobutene and Methanol (in Accordance with the Invention)

In the same apparatus as in Example 5, MTBE was cleaved at 250° C. The catalyst used was 10 g of the tablets prepared in Example 4. The throughput was 100 g of MTBE per hour. This corresponded to a WHSV of 10 h$^{-1}$. The experiment ran over 480 hours. The experimental results were compiled in Table 2.

TABLE 2

Conversions and selectivities of the cleavage of MTBE according to Example 6

| | Experimental duration (h) | | |
|---|---|---|---|
| | 48 | 144 | 480 |
| MTBE conversion (%) | 86.9 | 80.2 | 67.4 |
| Isobutene selectivity (%) | 99.7 | 99.8 | 99.9 |
| Methanol selectivity (%) | 99.27 | 99.29 | 99.12 |

The experiment shows that the tabletted catalyst from Example 4 has a higher activity than the catalyst from Example 2. The selectivity of methanol formation is better and the isobutene formation is somewhat lower than in the case of the catalyst from Example 2, but still outstanding. This catalyst too is suitable for the industrial preparation of isobutene by cleaving MTBE. Owing to the high activity of the catalyst, only a relatively small catalyst volume is required.

The invention claimed is:

1. A process for preparing isoolefins having 4 to 6 carbon atoms of the formula I

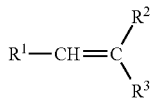

by catalytic gas phase cleavage of a starting compound of the formula II

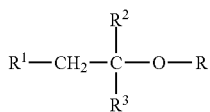

to give a compound of the formula I and a compound of the formula III

  R—OH  III wherein, in the formulae I to III, the R radical is H or an alkyl radical having 1, 2 or 3 carbon atom(s), the $R^1$ radical is H or a methyl or ethyl radical, and the $R^2$ and $R^3$ radicals are each methyl or ethyl radicals, where the $R^2$ and $R^3$ radicals may be the same or different, at a temperature of 110 to 450° C. and a pressure of 0.1 to 2 MPa, wherein the catalyst used in the gas phase cleavage comprises:
(i) 0.5 to 20% by mass of a member selected from the group consisting of MgO, or a mixture of an alkaline earth metal oxide and MgO;
(ii) 4 to 30% by mass of aluminum oxide; and
(iii) 60 to 95% by mass of silicon dioxide;
wherein a mean pore diameter of the catalyst is from 5 to 20 nm;
wherein at least 50% of the total pore volume of the catalyst is accounted for by mesopores having a diameter of 3.5 to 50 nm; and
wherein the total pore volume is a sum of the pore volume of the pores having a pore diameter of greater than or equal to 3.5 nm determined by mercury porosimetry according to DIN 66133.

2. The process according to claim 1, wherein over 70% of the total pore volume of the catalyst is accounted for by mesopores having a diameter of 3.5 to 50 nm.

3. The process according to claim 1, wherein the compound II cleaved is tert-butanol to isobutene as the compound of the formula I and water as the compound III.

4. The process according to claim 1, wherein R in said compound of formula II is a methyl, ethyl or propyl radical.

5. The process according to claim 4, wherein methyl tert-butyl ether is cleaved to isobutene and methanol, or ethyl tert-butyl ether to isobutene and ethanol.

6. The process according to claim 1, wherein the catalyst comprises 5 to 15% by mass of magnesium oxide, 10 to 20% by mass of aluminum oxide, and 70 to 90% by mass of silicon dioxide.

7. The process according to claim 1, wherein the catalyst has a BET surface area of 200 to 450 $m^2/g$.

8. The process according to claim 1, wherein the catalyst has a pore volume of 0.5 to 1.3 ml/g.

9. The process according to claim 1, wherein the mean pore diameter of the catalyst is 8 to 15 nm.

10. The process according to claim 1, wherein the catalyst has a longest dimension of from 10 μm to 10 mm.

11. A process for preparing isoolefins having 4 to 6 carbon atoms of the formula I

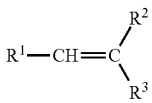

by catalytic gas phase cleavage of a starting compound of the formula II

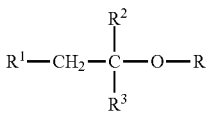

to give a compound of the formula I and a compound of the formula III

  R—OH  III wherein, in the formulae I to III, the R radical is H or an alkyl radical having 1, 2 or 3 carbon atom(s), the $R^1$ radical is H or a methyl or ethyl radical, and the $R^2$ and $R^3$ radicals are each methyl or ethyl radicals, where the $R^2$ and $R^3$ radicals may be the same or different, at a temperature of 110 to 450° C. and a pressure of 0.1 to 2 MPa, wherein the catalyst used in the gas phase cleavage comprises:
(i) 0.5 to 20% by mass of a member selected from the group consisting of MgO, or a mixture of an alkaline earth metal oxide and MgO;
(ii) 4 to 30% by mass of aluminum oxide; and
(iii) 60 to 95% by mass of silicon dioxide;
wherein a mean pore diameter of the catalyst is from 5 to 20 nm;
wherein at least 50% of the total pore volume of the catalyst is accounted for by mesopores having a diameter of 3.5 to 50 nm;
wherein the total pore volume is a sum of the pore volume of the pores having a pore diameter of greater than or equal to 3.5 nm determined by mercury porosimetry according to DIN 66133; and
wherein said catalyst does not comprise a heavy metal.

12. The process according to claim 11, wherein the compound II cleaved is tert-butanol to isobutene as the compound of the formula I and water as the compound III.

13. The process according to claim 11, wherein R in said compound of formula II is a methyl, ethyl or propyl radical.

14. The process according to claim 13, wherein methyl tert-butyl ether is cleaved to isobutene and methanol, or ethyl tert-butyl ether to isobutene and ethanol.

15. The process according to claim 11, wherein the catalyst comprises 5 to 15% by mass of magnesium oxide, 10 to 20% by mass of aluminum oxide, and 70 to 90% by mass of silicon dioxide.

16. The process according to claim 11, wherein the catalyst has a BET surface area of 200 to 450 $m^2/g$.

17. The process according to claim 11, wherein the catalyst has a pore volume of 0.5 to 1.3 ml/g.

18. The process according to claim 11, wherein the mean pore diameter of the catalyst is 8 to 15 nm.

19. The process according to claim 11, wherein the catalyst has a longest dimension of from 10 μm to 10 mm.

20. A process for preparing isoolefins having 4 to 6 carbon atoms of the formula I

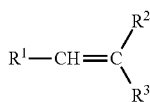

I by catalytic gas phase cleavage of a starting compound of the formula II

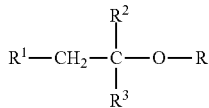

II to give a compound of the formula I and a compound of the formula III

  III wherein, in the formulae I to III, the R radical is H or an alkyl radical having 1, 2 or 3 carbon atom(s), the $R^1$ radical is H or a methyl or ethyl radical, and the $R^2$ and $R^3$ radicals are each methyl or ethyl radicals, where the $R^2$ and $R^3$ radicals may be the same or different, at a temperature of 110 to 450° C. and a pressure of 0.1 to 2 MPa, wherein
the catalyst used in the gas phase cleavage comprises:
(i) 0.5 to 20% by mass of a member selected from the group consisting of MgO, or a mixture of an alkaline earth metal oxide and MgO;
(ii) 4 to 30% by mass of aluminum oxide; and
(iii) 60 to 95% by mass of silicon dioxide;
wherein a mean pore diameter of the catalyst is from 5 to 20 nm;
wherein at least 50% of the total pore volume of the catalyst is accounted for by mesopores having a diameter of 3.5 to 50 nm;
wherein the total pore volume is a sum of the pore volume of the pores having a pore diameter of greater than or equal to 3.5 nm determined by mercury porosimetry according to DIN 66133;
wherein said catalyst does not comprise a heavy metal; and
wherein a conversion rate of the compound of formula II is more than 70% and the selectivity of formation of the isoolefin of formula I is over 99%.

21. The process according to claim 20, wherein the compound II cleaved is tert-butanol to isobutene as the compound of the formula I and water as the compound III.

22. The process according to claim 20, wherein R in said compound of formula II is a methyl, ethyl or propyl radical.

23. The process according to claim 22, wherein methyl tert-butyl ether is cleaved to isobutene and methanol, or ethyl tert-butyl ether to isobutene and ethanol.

24. The process according to claim 20, wherein the catalyst comprises 5 to 15% by mass of magnesium oxide, 10 to 20% by mass of aluminum oxide, and 70 to 90% by mass of silicon dioxide.

25. The process according to claim 20, wherein the catalyst has a BET surface area of 200 to 450 m²/g.

26. The process according to claim 20, wherein the catalyst has a pore volume of 0.5 to 1.3 ml/g.

27. The process according to claim 20, wherein the mean pore diameter of the catalyst is 8 to 15 nm.

28. The process according to claim 20, wherein the catalyst has a longest dimension of from 10 μm to 10 mm.

* * * * *